(12) United States Patent
De Haan et al.

(10) Patent No.: US 8,547,089 B2
(45) Date of Patent: Oct. 1, 2013

(54) METHOD OF NON-DESTRUCTIVELY TESTING, A SYSTEM AND A COMPUTER PROGRAM PRODUCT

(75) Inventors: Victor Otto De Haan, Puttershoek (NL); Paul Andre De Jong, Vlaardingen (NI); Thomas Theodorus Arnoldus Van Overbeek, Delft (NL)

(73) Assignee: Rontgen Technische Dienst B.V., Rotterdam (NL)

( * ) Notice: Subject to any disclaimer, the term of this patent is extended or adjusted under 35 U.S.C. 154(b) by 472 days.

(21) Appl. No.: 12/801,159

(22) Filed: May 25, 2010

(65) Prior Publication Data

US 2010/0315077 A1 Dec. 16, 2010

(30) Foreign Application Priority Data

May 25, 2009 (NL) ...................................... 2002921

(51) Int. Cl.
*G01R 33/12* (2006.01)
*G01N 27/82* (2006.01)

(52) U.S. Cl.
USPC .......................................... 324/228; 324/240

(58) Field of Classification Search
None
See application file for complete search history.

(56) References Cited

U.S. PATENT DOCUMENTS

| | | | | |
|---|---|---|---|---|
| 3,597,678 A | * | 8/1971 | Fearon | 324/220 |
| 3,866,190 A | * | 2/1975 | de Jonge et al. | 365/20 |
| 6,366,083 B1 | * | 4/2002 | McClelland | 324/230 |

FOREIGN PATENT DOCUMENTS

| | | |
|---|---|---|
| EP | 1 085 526 | 3/2001 |
| WO | WO 98/34104 | 8/1998 |
| WO | WO 02/16921 | 2/2002 |
| WO | WO 2008/046209 | 4/2008 |

OTHER PUBLICATIONS

Dutch Search Report dated Mar. 30, 2010.

* cited by examiner

*Primary Examiner* — Vinh Nguyen
(74) *Attorney, Agent, or Firm* — Jacobson Holman PLLC (57) ABSTRACT

A method of non-destructively testing a magnetisable conducting object surrounded by a magnetisable layer wherein the field strength of a primary magnetic field that is applied exterior to the magnetisable layer is abruptly changed. A vanishing secondary magnetic field generated by eddy currents induced by the changed field strength of the primary magnetic field is received and the temporal field strength of the received secondary magnetic field is analysed for deriving characteristics of the magnetisable conducting object. Furthermore, a transient tertiary magnetic field exterior to the magnetisable layer when the field strength of the primary magnetic field abruptly changes is applied wherein the orientation of the primary and tertiary magnetic field, respectively, are mutually opposite.

7 Claims, 7 Drawing Sheets

METHOD OF NON-DESTRUCTIVELY TESTING, A SYSTEM AND A COMPUTER PROGRAM PRODUCT

This application has a priority of The Netherlands no. 2002921 filed May 25, 2009, hereby incorporated by reference.

The invention relates to a method of non-destructively testing a magnetisable conducting object mechanically shielded by a magnetisable layer, comprising the steps of abruptly changing a field strength of a primary magnetic field that is applied exterior to the magnetisable layer, receiving a vanishing secondary magnetic field generated by eddy currents induced by the changed field strength of the primary magnetic field, and analyzing a temporal field strength of the received secondary magnetic field for deriving characteristics of the magnetisable object.

Magnetic fields are widely used for non-destructively testing magnetisable conducting objects, such as pipe lines or metal plates, e.g. for corrosion or cracks. Thereto, the magnetisable object is probed by a primary magnetic field that is suddenly switched off, thereby inducing eddy currents in the object. Subsequently, the eddy currents generate a secondary magnetic field that may be measured to find characteristics of the tested object, such as local wall thickness.

However, when the magnetisable object is mechanically shielded by a layer that is also magnetisable, it becomes difficult to retrieve object characteristics from the secondary magnetic field since eddy currents or other transient magnetic effects in the shielding layer cause an additional field that interferes with the secondary field.

It is an object of the invention to provide a method according to the preamble wherein improved testing results may be obtained when testing magnetisable conducting objects that are mechanically shielded by a magnetisable layer. Thereto, the method according to the invention further comprises the step of applying a transient tertiary magnetic field exterior to the magnetisable layer when the field strength of the primary magnetic field abruptly changes, wherein the orientation of the primary and tertiary magnetic field, respectively, are mutually opposite.

The invention is partly based in the insight that the eddy currents in the magnetisable layer generate a field that not merely superposes to the secondary magnetic field generated by the eddy currents in the object, but also interferes with the eddy current behaviour in the object itself. The interference with the eddy currents in the object blurs the secondary magnetic field and reduces the applicability. More importantly, relaxation mechanisms in the shielding layer interfere with the secondary magnetic field, thus providing a noisy signal that covers information of object characteristics.

By applying an oppositely oriented tertiary magnetic field at the instant when the primary magnetic field abruptly changes, the effect of eddy currents in the magnetisable layer reduces dramatically. Magnetic domains in the magnetisable layer are realigned and neutralized so that further relaxations are prevented and have a reduced effect on the eddy currents in the object and on the secondary magnetic field to be measured. As such, the method according to the invention enables non-destructive testing of magnetisable conducting objects that are shielded with a magnetisable layer wherein the effect of the magnetisable layer is virtually removed.

In a preferred embodiment according to the invention, the duration of the transient tertiary magnetic field is shorter than a time instant corresponding to a temporal field strength behaviour associated with a magnetisable object characteristic. As a result, object characteristics can be measured without substantial interference of the tertiary magnetic field with the object.

Advantageously, the tertiary magnetic field is strong enough for substantially neutralizing relaxation processes in the magnetisable layer, so that influence on eddy currents creating the secondary magnetic field is minimized. Obviously, the tertiary magnetic field may be also be chosen smaller, e.g. to reduce the effects of the relaxation process in the magnetisable layer while improving the chance that the tertiary magnetic field does not interact with the eddy currents in the object.

Further, the tertiary magnetic field may be chosen weak enough for avoiding substantial interaction with temporal eddy currents in the magnetisable conducting object, thus counteracting undesired interaction with the secondary magnetic field. The primary magnetic field that is applied exterior to the magnetisable layer may for example be in the form of a steady magnetic field which is suddenly switched off pulse or in the form of a pulse (a magnetic fields which is switched on and off).

Further, the invention relates to a system.

Additionally, the invention relates to a computer program product. A computer program product may comprise a set of computer executable instructions stored on a data carrier, such as a CD or a DVD. The set of computer executable instructions, which allow a programmable computer to carry out the method as defined above, may also be available for downloading from a remote server, for example via the Internet.

Other advantageous embodiments according to the invention are described in the following claims.

By way of example only, embodiments of the present invention will now be described with reference to the accompanying figures in which.

The figures are merely schematic views of preferred embodiments according to the invention. In the figures, the same reference numbers refer to equal or corresponding parts.

Figure 1:
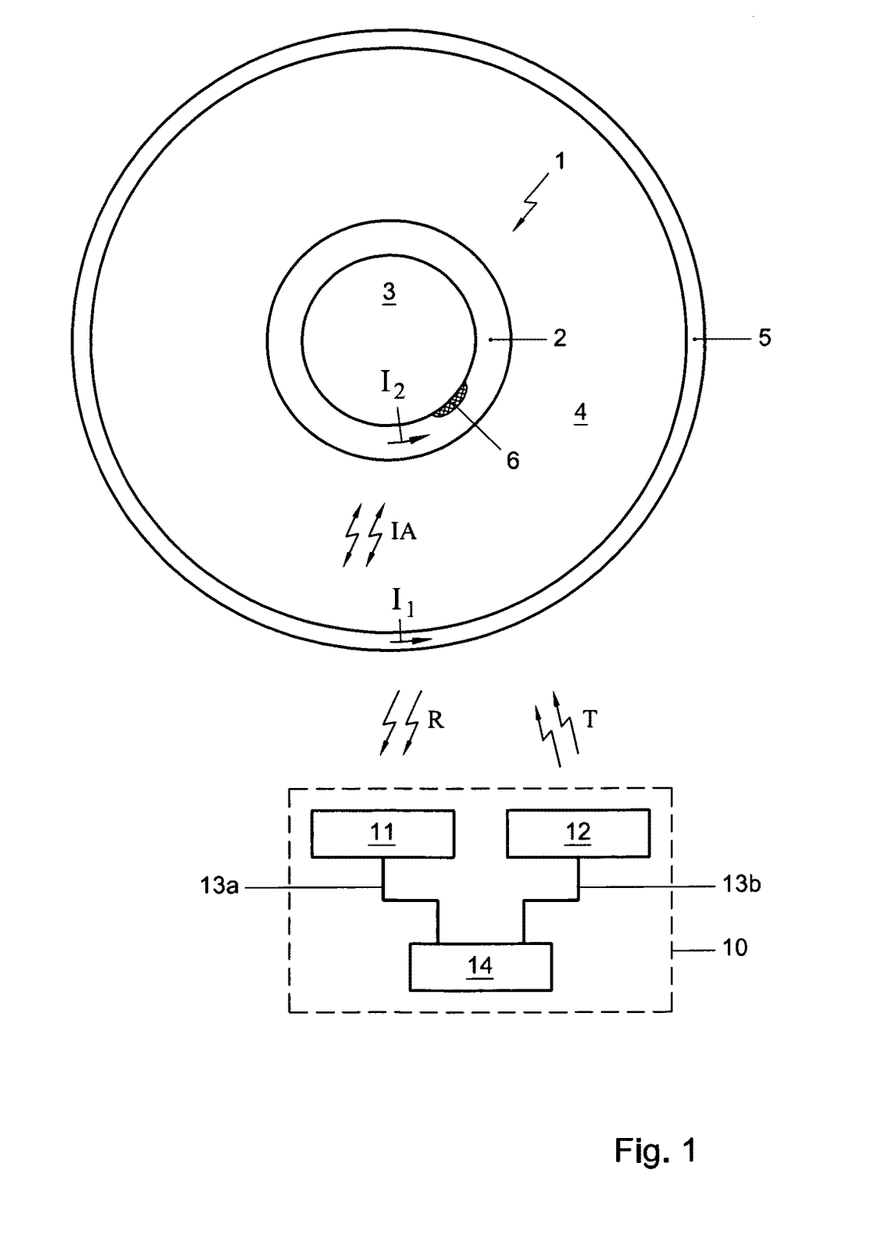
FIG. 1 shows a schematic view of a system according to the invention.

FIG. 1 shows a view of a system 10 according to the invention. The system 10 comprises a magnetic field receiver 11, a magnetic field source unit 12 and a processor 14 that is connected to the receiver 11 and the source 12 via data lines 13a-b, respectively. FIG. 1 further shows a cross sectional view of a magnetisable conducting object 1 to be tested. The object 1 includes a pipe 2 enclosing a channel 3. The object 1 is mechanically shielded or covered by an enclosing magnetisable cylindrical layer 5 spaced from the object, thus defining an intermediate space 4 between the shielding layer 5 and the outer surface of the pipe 2. The pipe 2 is provided with a corrosion area 6 effectively locally narrowing the pipe thickness.

During operation of the system 1 according to the invention, the processor 14 provides a first signal for transmission to the magnetic field source unit 12 for abruptly changing the field strength of a primary magnetic field. The magnetic field source unit 12 is arranged for generating a primary magnetic field T for application exterior to the magnetisable layer 5. By applying the primary magnetic field, magnetization of the magnetisable conducting object 1 and the magnetisable layer 5 is obtained. Upon receipt of said first signal, the magnetic field source unit 12 abruptly changes the field strength of the primary magnetic field T, thereby inducing eddy currents in the magnetisable conducting object 1. The eddy currents generate a vanishing secondary magnetic field R that is received by the magnetic field receiver 11. The primary magnetic field that is applied exterior to the magnetisable layer may for example be in the form of a steady magnetic field which is suddenly switched off or in the form of a pulse (a magnetic fields which is switched on and shortly thereafter (for example after 1 second) is switched off). Then, the magnetic field receiver 11 generates a second signal representing the vanishing secondary magnetic received field R. The second signal is input to the processor 14 for analyzing the temporal field strength of the received secondary magnetic field R, so that characteristics of the magnetisable conducting object 1 can be derived.

Deriving object characteristics from said temporal field strength can be performed in various ways, e.g. by determining one or more bends in a field strength curve and/or by matching a field strength curve to a corresponding model.

In a practical embodiment, the primary field is turned on until a steady state is reached. Then, the primary magnetic field is switched off thereby abruptly changing the primary magnetic field and inducing the eddy currents $I_1$; $I_2$ in the layer 5 and in the object 1. As an alternative, the primary magnetic field is abruptly switched on to obtain the abrupt change in the primary magnetic field.

It is noted that the magnetisable layer needs not to be electrically conductive. If the layer is not conductive the method according to the invention can still be applied. According to an aspect of the invention, not eddy currents are suppressed, as the eddy currents would not have, due to the small thickness of the layer, a significant influence on the measurements of thicker magnetisable conducting objects. However, according to an aspect of the invention, the influence of the relaxation mechanism occurring in the shielding magnetisable layer is reduced or suppressed.

It is further noted that the magnetic field source unit 12 in the shown embodiment comprises a single transmitting element for transmitting both the primary magnetic field and a tertiary magnetic field to be discussed hereafter. The single transmitting element is e.g. implemented as a coil. When an electrical current flows through the coil, a magnetic field is generated. In fact, the single transmitting element is controlled to generate the abruptly changing primary field and the oppositely oriented tertiary field. However, as an alternative, the magnetic field source unit 12 might include two separate transmitting elements wherein a first transmitting element transmits the primary magnetic field while a second transmitting element transmits the tertiary magnetic field.

Also the magnetic field receiver 11 might be implemented as a coil. Obviously, the secondary magnetic field can also be embodied otherwise, e.g. as a Hall sensor or a GMR sensor.

When the magnetic field source unit 12 is turned on to magnetise the object 1 under investigation also the magnetisable layer 5, optionally embodied as a galvanized sheeting, is magnetized. As soon as possible magnetic domains of the magnetisable layer 5 try to align with the applied field. To start the testing measurement, the primary magnetic field is switched off, after which the decay of the eddy currents in the investigated object 1 is measured by the receiver 11. At the same time the magnetic domains in the magnetisable layer 5 are released from their forced alignment and start to realign according to a locally preferred energy state. The realignment will take some time resulting in a changing magnetic field due to the domain realignment until a final remanence state is reached. The above-described physical phenomenon is known as relaxation of magnetic domains. The changing magnetic field results in an interaction signal IA due to magnetisable layer.

Figure 2:
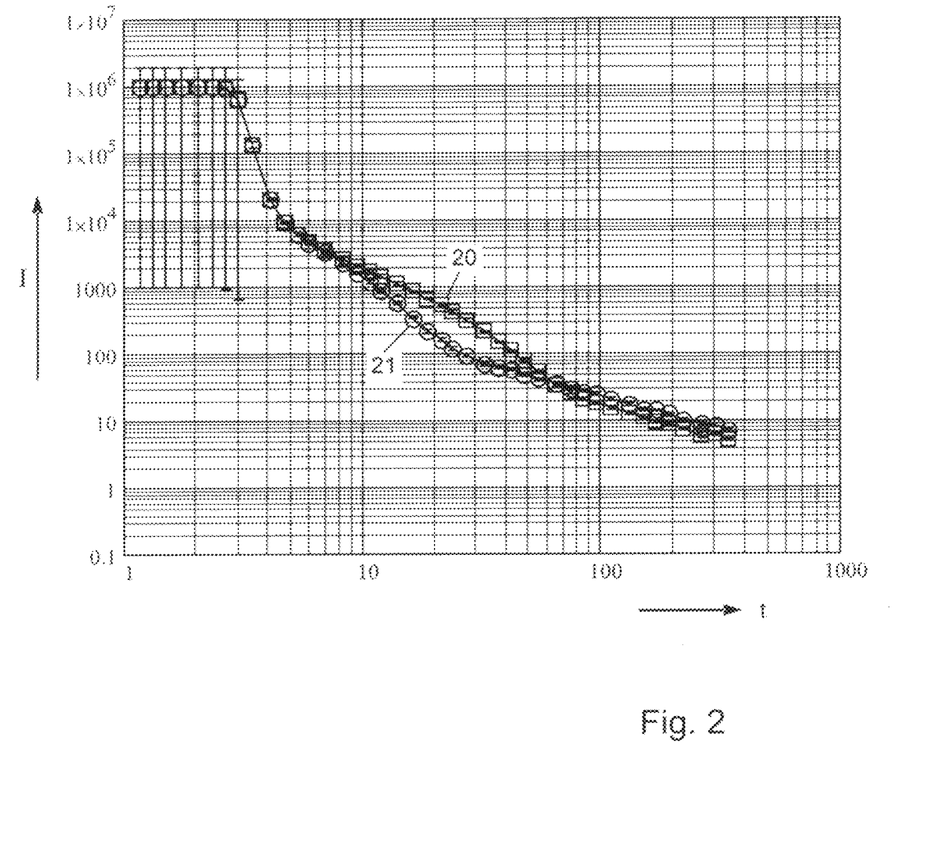
FIG. 2 shows a first diagram of received secondary magnetic fields.

FIG. 2 shows a first diagram of received secondary magnetic fields

I plotted as a function of time t[s] on a double logarithmic diagram. The object 1 is a pipe 2 shielded by a galvanized sheeting 5. A first curve 20 represents a normal situation wherein the pipe has a constant nominal thickness, while a second curve 21 represents a situation wherein the pipe thickness is reduced by circa 50%. Although for the shown curves, the reduction of the wall thickness is still observable, a normal clear bend at a time instant corresponding with the wall thickness is obscured by the intermediate signal IA generated by the galvanized sheeting. Analysis of the curve tail at relatively high time instants becomes difficult. Obviously, the bend in the curve due to the wall thickness would become invisible for thicker materials, as the curve decays according to $t^{\gamma 1}$, where $\gamma 1 \approx -1.5$ and a relaxation signal decays according to $t^{\gamma 2}$ where $\gamma 2 \approx -1$.

Typically, the relaxation mechanism is an unforced relaxation: there is no external driving force, only local energy gain or loss that drives the relaxation. This opens up the possibility to reduce the galvanized sheeting relaxation signal. When the domains are forced to realign by means of an external force, the signal due to the reorientation can be reduced. To accomplish this, directly after switching off the current through the transmitter coil 12, a voltage is applied with opposite polarity as was needed to send the current through the coil. This enables to build a third, countering magnetic field inside the sheeting 5. When the third magnetic field becomes high enough, the domains are forced to realign again. Preferably, the pulse is chosen in such a way that it contains as much energy as is needed to realign substantially half of the domains. Since the domains are of different size and need a slightly different force or energy to realign, substantially half of the domains can be realigned. Then, the further relaxation process will go on substantially unnoticed by the receiver system as the domains with opposite alignments will relax in a manner opposite to the realigned domains. As a result, the net sum of magnetic fields have a much smaller influence on the signal, in the ideal case the magnetic fields in the shielding layer have a net nil effect.

Thereto, according to an aspect of the invention, the processor 14 provides a third signal for applying a transient tertiary magnetic field exterior to the magnetisable layer 5 when the field strength of the primary magnetic field abruptly changes, wherein the orientation of the primary and tertiary magnetic field, respectively, are mutually opposite. Said third signal is transmitted to the magnetic field source unit 12 to actually generate the transient tertiary magnetic field.

Figure 3:
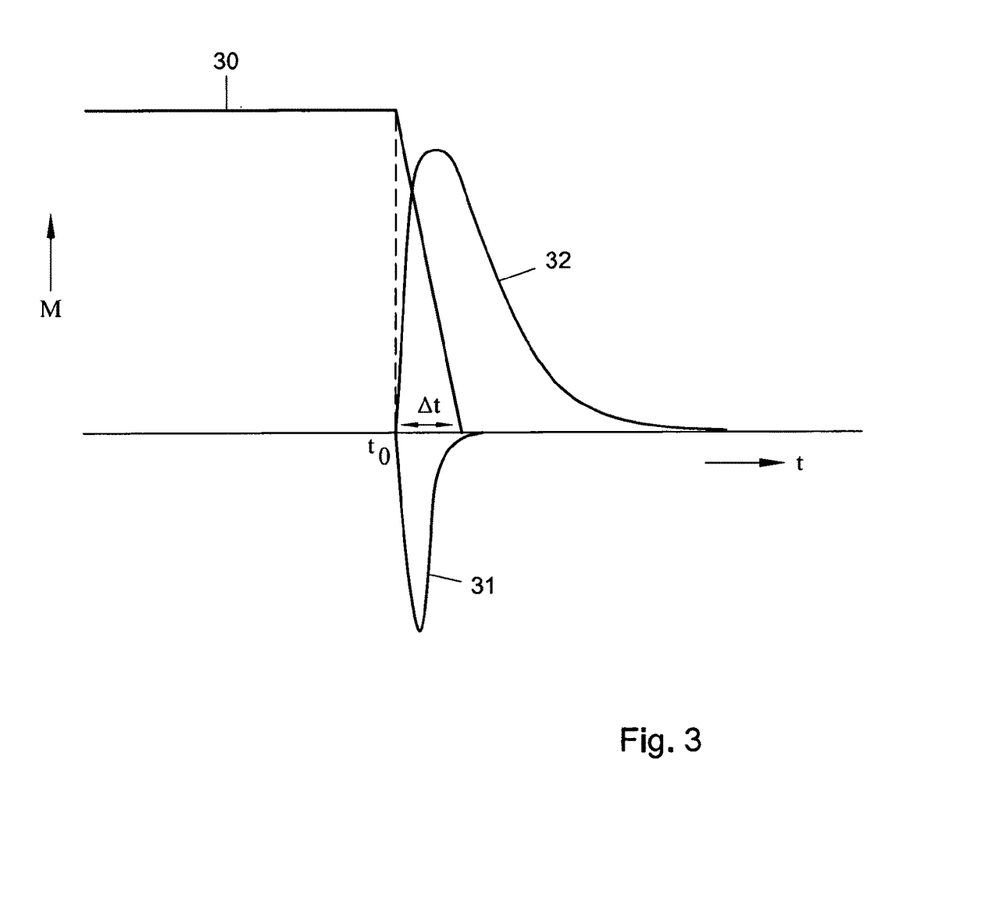
FIG. 3 shows a diagram of transmitted magnetic fields.

FIG. 3 shows a diagram of transmitted magnetic fields M as a function of time t. A primary magnetic field 30 is switched off at a time instant $t_0$ to start the test measurement. The primary magnetic field 30 has a finite fall down time period $\Delta t$. FIG. 3 further shows a tertiary magnetic field 31 having opposite orientation with respect to the primary magnetic field orientation. As an example, when the primary magnetic field 30 has a positive sign, the tertiary magnetic field 31 has a negative sign, and vice versa. The tertiary magnetic field is also called the reverse signal. In addition, FIG. 3 shows a secondary vanishing magnetic field 32 that is caused by the eddy currents in the object 1. In this respect it is noted that the figure shows a scalar magnetic field component that represents a particular magnetic polarization. It is further noted that the secondary magnetic field curve is plotted on a scale that is different from the primary and tertiary magnetic field scales.

The duration of the transient tertiary magnetic field is shorter than a time instant corresponding to a temporal field strength behaviour associated with a magnetisable conducting object characteristic. More specifically, the transient tertiary magnetic field vanishes before a tail of the secondary magnetic field starts, in which tail information of the magnetisable object 1 can be retrieved.

Further, the tertiary magnetic field is strong enough for substantially neutralizing temporal relaxation effects in the magnetisable layer 5. Also, the tertiary magnetic field is weak enough for avoiding substantial interaction with temporal eddy currents in the magnetisable conducting object 1.

The transient tertiary magnetic field may be pulse shaped. As the reverse pulse can be a voltage excitation of the transmitter coil, the build up of current through the coil and the magnetic field in the sheeting depends on the self-induction of the transmitter coil. This enables the control of the applied magnetic field by changing the period of the reverse pulse. Obviously, if the reverse pulse would be applied for a period as long as the secondary magnetic field, the complete signal will have been reversed and the reverse pulse does not have any improved measurement effect. Hence, the reverse pulse must be long enough to force at least part of the domains to realign and short enough so that is does not considerably changes the secondary magnetic field.

Figure 4:
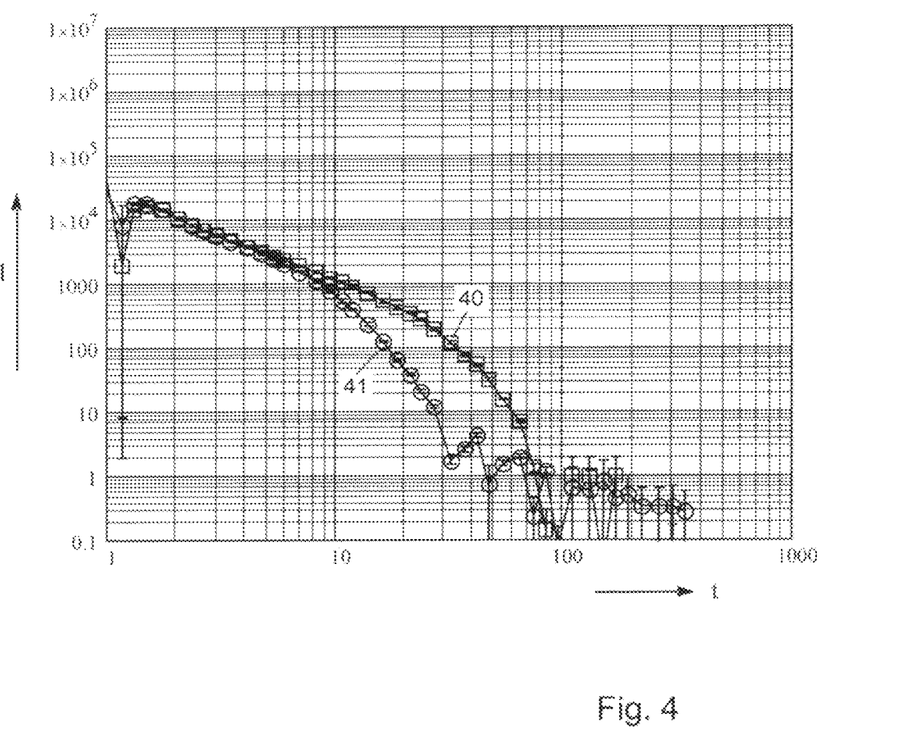
FIG. 4 shows a second diagram of received secondary magnetic fields.

FIG. 4 shows a second diagram of received secondary magnetic fields I plotted as a function of time t[s] on a double logarithmic diagram. Again, the diagram shows a first curve 40 representing a normal situation wherein the pipe has a constant nominal thickness, while a second curve 41 represents a situation wherein the pipe thickness is reduced by circa 50%. Here, the curves 40, 41 have been obtained while applying the transient tertiary magnetic field. In particular, the effect of a reverse pulse of 1.38 ms on the before measured cases is shown. The tail of the galvanized sheeting is almost completely compensated. The bends due to the wall thickness of the object are clearly visible and comparable with the behaviour under aluminium sheeting.

Figure 5:
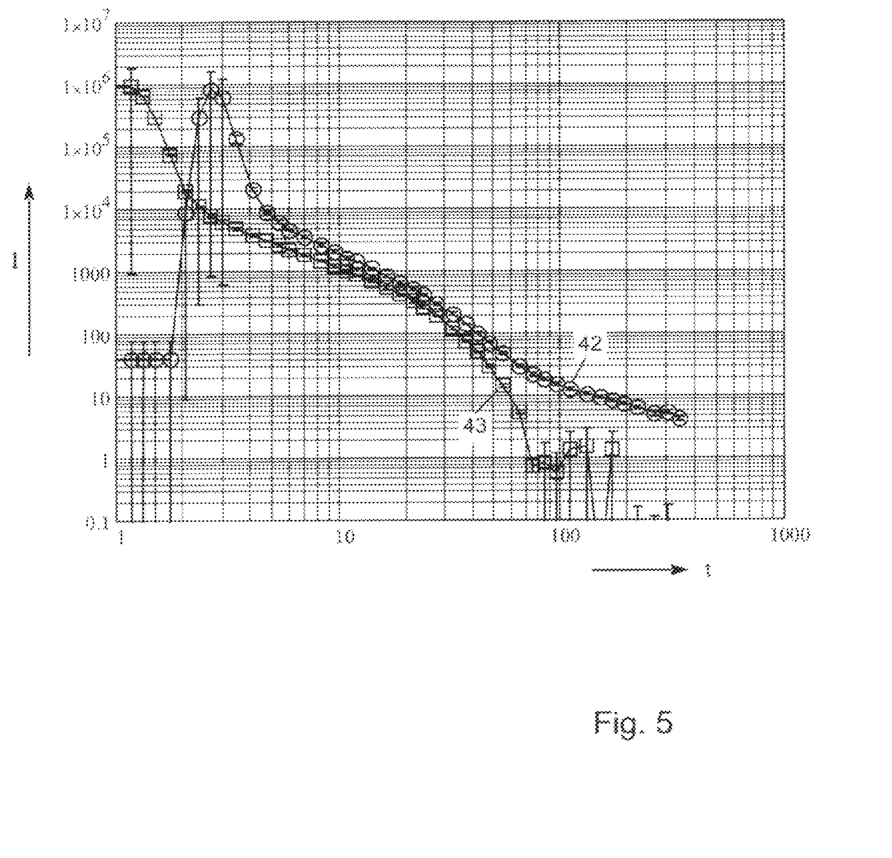
FIG. 5 shows a third diagram of received secondary magnetic fields.
Figure 6:
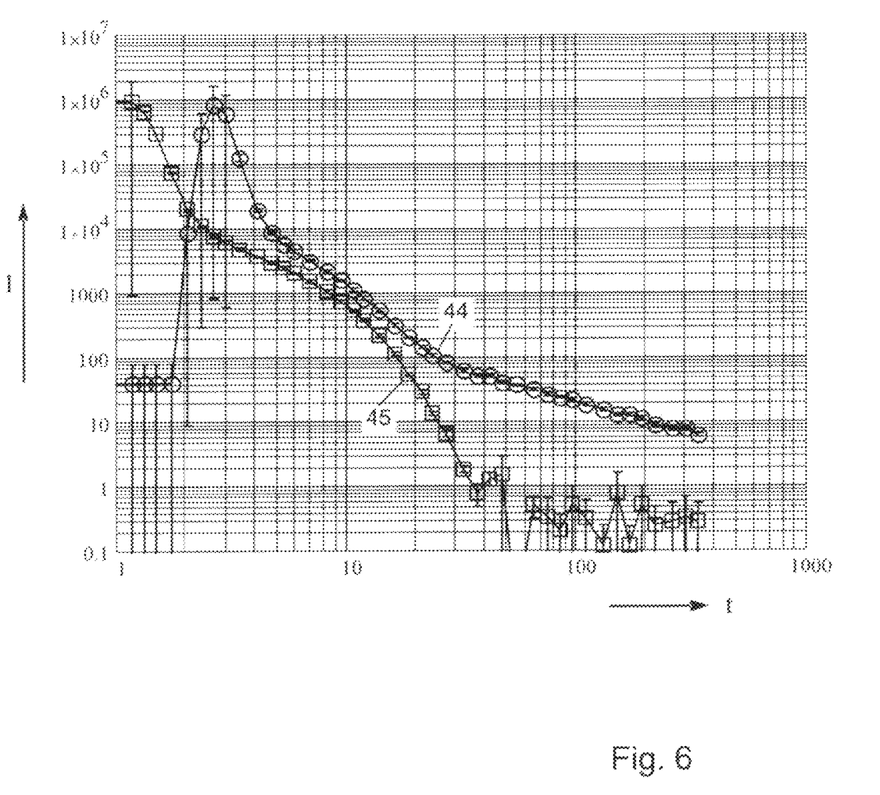
FIG. 6 shows a fourth diagram of received secondary magnetic fields.

FIGS. 5 and 6 show a third and fourth diagram, respectively, of received secondary magnetic fields I plotted as a function of time t[s] on a double logarithmic diagram. Here, the object is a plate. The influence of the reverse pulse on the secondary magnetic field wherein the plate has a wall thickness of 12 mm is shown in FIG. 5. A lift-off, i.e. a distance between the object 1 and the layer 5, of 75 mm is applied. A first curve 42 represents the situation without applied reverse pulse, while a second curve 43 represents the situation wherein the reverse pulse is applied according to an aspect of the invention. As shown, when applying the reverse pulse, the amplitude of the measured secondary magnetic field is reduced to approximately 55%. The tail due to the galvanized sheeting has been reduced by at least a factor of 20. A comparable situation arise for the measurements on a wall thickness of 6 mm. FIG. 6 shows similar curves 44, 45 where the secondary magnetic field amplitude is reduced to approximately 50%. The tail due to the galvanized sheeting has been reduced by at least a factor of 60.

The long time tail in the signal arising from the relaxation of the domains in galvanized sheeting can be compensated for by means of a reverse voltage pulse of appropriate time length. The reverse pulse may reduce the amplitude of this tail by at a factor 20 to 60. Further, the pulse may reduce the signal of the object by roughly a factor of 2. The reverse pulse also reduces the induction signal of a probe, i.e. the signal without object 1 of layer 5 close to the probe, by roughly a factor of 2 compared to its value in a situation wherein no reverse pulse is applied. The method according to the invention enables non-destructive testing of magnetisable conducting objects that are shielded with a magnetisable layer wherein the effect of the magnetisable layer is virtually removed.

Figure 7:
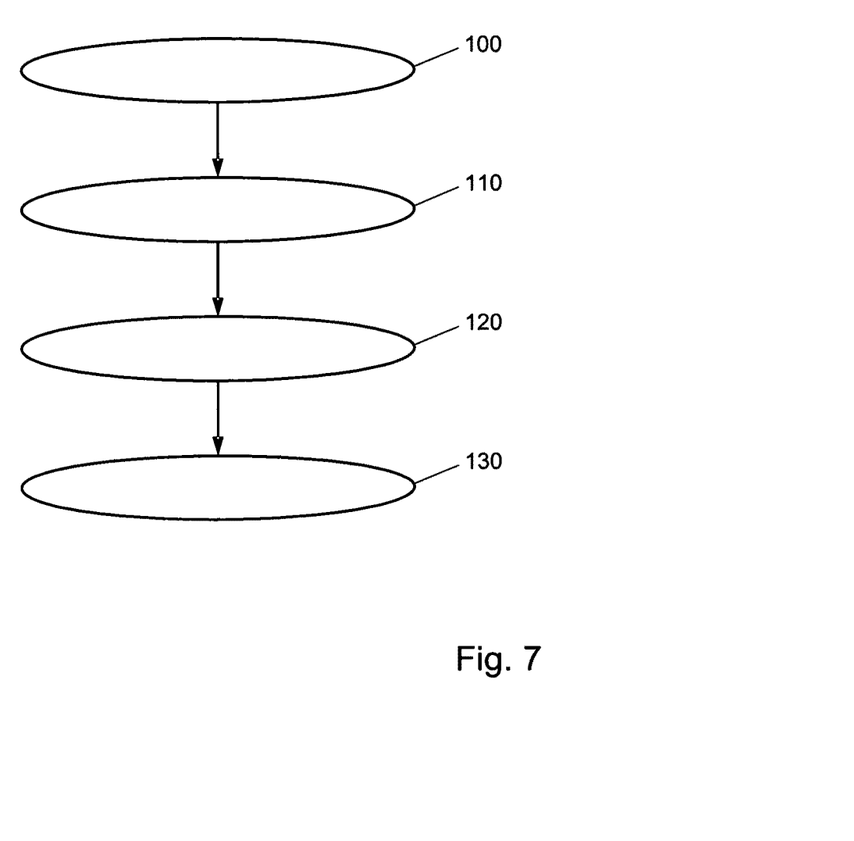
FIG. 7 shows a flow chart of an embodiment of a method according to the invention.

FIG. 7 shows a flow chart of an embodiment of the method according to the invention. The method is used for non-destructively testing a magnetisable conducting object mechanically shielded by a magnetisable layer. The method comprises the steps of abruptly changing (100) a field strength of a primary magnetic field that is applied exterior to the magnetisable layer, applying (110) a transient tertiary magnetic field exterior to the magnetisable layer when the field strength of the primary magnetic field abruptly changes, wherein the orientation of the primary and tertiary magnetic field, respectively, are mutually opposite, receiving (120) a vanishing secondary magnetic field generated by eddy currents induced by the changed field strength of the primary magnetic field, and analyzing (130) a temporal field strength of the received secondary magnetic field for deriving characteristics of the magnetisable object.

The method of non-destructively testing a magnetisable object mechanically shielded by a magnetisable layer can be performed using dedicated hardware structures, such as FPGA and/or ASIC components. Otherwise, the method can also at least partially be performed using a computer program product comprising instructions for causing a processor of a computer system to perform the above described steps of the method according to the invention. All processing steps can in principle be performed on a single processor. However it is noted that at least one step can be performed on a separate processor, e.g. the step of receiving the vanishing secondary magnetic field and/or the step of analyzing the temporal field strength.

The invention is not restricted to the embodiments described herein. It will be understood that many variants are possible.

The system and method according to the invention can not merely be applied to pipe segments surrounded by magnetisable layers, but also to other magnetisable conducting objects that are mechanically shielded by a magnetisable layer, such as a plate that is shielded by a plane sheet. In this context it is noted that the object might in principle have any geometry, such as a plate, a cylinder or a ball shell. Also the shielding magnetisable layer geometry may vary. The layer may e.g. be curved or substantially plane.

Other such variants will be obvious for the person skilled in the art and are considered to lie within the scope of the invention as formulated in the following claims.

The invention claimed is:

1. A method of non-destructively testing a magnetisable conducting object mechanically shielded by a magnetisable layer, comprising the steps of:
   abruptly changing a field strength of a primary magnetic field that is applied exterior to the magnetisable layer thereby inducing eddy currents in the object,
   receiving a vanishing secondary magnetic field generated by eddy currents induced by the changed field strength of the primary magnetic field,
   analyzing a temporal field strength of the received secondary magnetic field for deriving characteristics of the magnetisable conducting object, and applying a transient tertiary magnetic field exterior to the magnetisable layer when the field strength of the primary magnetic field abruptly changes, wherein the orientation of the primary and tertiary magnetic field, respectively, are mutually opposite and the tertiary magnetic field is strong enough for substantially neutralizing temporal relaxation processes in the magnetisable layer thereby allowing the testing.

2. The method according to claim 1, wherein the duration of the transient tertiary magnetic field is shorter than a time instant corresponding to a temporal field strength behaviour associated with a magnetisable conducting object characteristic.

3. The method according to claim 1, wherein the tertiary magnetic field is weak enough for avoiding substantial interaction with temporal eddy currents in the magnetisable conducting object.

4. The method according to claim 1, wherein the step of abruptly changing the primary magnetic field strength includes switching off the primary magnetic field.

5. A system for non-destructively testing a magnetisable conducting object mechanically shielded by a magnetisable layer, comprising:
    a magnetic field source unit for generating a primary magnetic field that is applied exterior to the magnetisable layer thereby inducing eddy currents in the object;
    a magnetic field receiver for receiving a vanishing secondary magnetic field generated by eddy currents;
    a processor arranged for transmitting a first signal to the magnetic field source unit for abruptly changing the field strength of the primary magnetic field,
    inputting a second signal from the magnetic field receiver, the second signal representing the vanishing secondary magnetic received field generated by eddy currents induced by the changed field strength of the primary magnetic field, and
    analyzing a temporal field strength of the received secondary magnetic field for deriving characteristics of the magnetisable conducting object,
    transmitting a third signal to the magnetic field source unit for applying a transient tertiary magnetic field exterior to the magnetisable layer when the field strength of the primary magnetic field abruptly changes, wherein the orientation of the primary and tertiary magnetic field, respectively, are mutually opposite and the tertiary magnetic field is strong enough for substantially neutralizing temporal relaxation processes in the magnetisable layer thereby allowing the testing.

6. The system according to claim 5, wherein the magnetic field source unit comprises a single transmitting element for transmitting both the primary magnetic field and the tertiary magnetic field.

7. The system according to claim 5, wherein the magnetic field source unit comprises two separate transmitting elements for transmitting the primary magnetic field and the tertiary magnetic field, respectively.

* * * * *